United States Patent [19]

Tsuji et al.

[11] Patent Number: 5,846,977

[45] Date of Patent: *Dec. 8, 1998

[54] NERVE GROWTH FACTOR PRODUCTION ACCELERATORS AND COMPOSITIONS FOR PREVENTING OR TREATING NEURONAL DEGENERATION

[75] Inventors: Tomoko Tsuji; Kohji Yamaguchi; Kiyosi Kondo, all of Kanagawa; Teizi Urakami, Tokyo, all of Japan

[73] Assignees: Mitsubishi Gas Chemical Company; Sagami Chemical Research Center, both of Tokyo, Japan

[ * ] Notice: The term of this patent shall not extend beyond the expiration date of Pat. No. 5,589,481.

[21] Appl. No.: 675,385

[22] Filed: Jul. 2, 1996

Related U.S. Application Data

[62] Division of Ser. No. 200,912, Feb. 22, 1994, Pat. No. 5,589,481, which is a continuation of Ser. No. 9,806, Jan. 27, 1993, abandoned.

[30] Foreign Application Priority Data

Feb. 7, 1992 [JP] Japan ....................................... 4-56677
Feb. 20, 1992 [JP] Japan ....................................... 4-69382

[51] Int. Cl.$^6$ ...................................................... A61K 31/44
[52] U.S. Cl. ............................................................... 514/292
[58] Field of Search ............................................... 514/292

[56] References Cited

U.S. PATENT DOCUMENTS 4,898,870  2/1990  Narutomi et al. ....................... 514/292
5,061,711  10/1991  Urakami et al. ........................ 514/292

*Primary Examiner*—Zohreh Fay
*Assistant Examiner*—M. Moezie
*Attorney, Agent, or Firm*—Klauber & Jackson

[57] ABSTRACT

Nerve growth factor production accelerating agents containing oxazopyrroloquinolines, pyrroquinolinequinones and/or their esters as active ingredient are provided. As the oxazopyrroloquinolines and their esters exhibit such production accelerating activity, they are suitably utilized for preventing and treating functional disorders of central nervous system, particularly, Alzheimer's dementia, cerebral ischemia and spinal trauma, as well as for functional disorders of peripheral nervous system, particularly, peripheral nervous system trauma and diabetic neurosis. As the pyrroquinolinequinones and their esters exhibit strong nerve growth factor production accelerating activity, they are suitably utilized for preventing and treating functional disorders of peripheral nervous system, particularly, peripheral nervous system trauma, diabetic neurosis, etc.

11 Claims, No Drawings

NERVE GROWTH FACTOR PRODUCTION ACCELERATORS AND COMPOSITIONS FOR PREVENTING OR TREATING NEURONAL DEGENERATION

This application is a divisional of application Ser. No. 08/200,912, filed Feb. 22, 1994, now U.S. Pat. No. 5,589,481, which is a continuation of application Ser. No. 08/009,806, filed Jan. 27, 1993, now abandoned.

This invention relates to pharmaceuticals, particularly, those for treating or preventing retrograde neural diseases, such as dementia senilis and Alzheimer's disease, and further to production accelerators for nerve growth factor (hereinafter referred to as NGF) which works for the recovery of neural function in central and peripheral nervous system diseases. Furthermore, it relates to compositions for preventing or treating neuronal degeneration.

NGF is a nutrition and growth factor necessary for the growth and maintenance of neuronal tissues, which is considered to be essential for maturation and differentiation of sensory and sympathetic nerves in the peripheral nervous system, and magnocellular cholinergic neurons in the central nervous system, as well as for life maintenance. It has, thus, been thought that the increase in the NGF level serves for the treatments of central functional disorders, such as Alzheimer's disease, vascular dementia and spinal trauma, and peripheral functional disorders, such as peripheral nervous trauma and diabetic neuronal disorders.

However, NGF is a protein with the molecular weight of 13,000 as monomer and 26,000 as dimer, so that it cannot pass through the blood-brain barrier. Accordingly, it has been thought preferable that an agent accelerating the production of NGF in the living body, rather than NGF itself, is administered to promote biosynthesis of NGF, thereby to improve disorders of the central and peripheral nervous systems. Thus, investigations to seek NGF production accelerators have been attempted.

Cathecholamines, such as epinephrine, norepinephrine and dopamine, have been found as agents having NGF production accelerating activity. However, because these compounds are a kind of hormones, their administration to accelerate the NGF synthesis is accompanied by some side effects due to quantitatively ill-balanced hormones in the living body. Therefore, satisfactory drugs have not yet been discovered from the practical point of view.

The present inventors have extensively studied on NGF production accelerating agents on account of the reasons as mentioned above, and accomplished the present invention, based upon the findings that oxazopyrroloquinolines, pyrroloquinolinequinones, and their esters exhibit in NGF production accelerating activity. Accordingly, the present invention provides NGF production accelerating agent containing an oxazopyrroloquinoline or pyrroloquinolinequinone and/or their esters as an ingredient.

The term, oxazopyrroloquinolines (hereinafter referred to as OPQs), used herein means 2,8,10-tricarboxy-1H-oxazo[5,4-h]-pyrrolo[2,3-f]quinolines (OPQ) and 5-substituted compounds thereof. The OPQs and their esters are represented by the following formula:

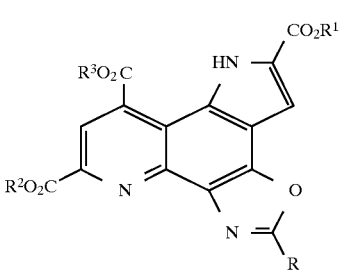

wherein R represents a hydrogen atom or an alkyl group having 1–4 carbon atoms, which may be substituted with a hydroxyl, carboxyl, mercapto, carbamoyl, hydroxyphenyl, guanidyl, imidazolyl, or methylmercapto group, and $R^1$, $R^2$ and $R^3$ represent a hydrogen atom or an alkyl alkenyl or benzyl group which may be same or different.

OPQs employed in the present invention can readily be prepared by a process wherein a pyrroloquinolinequinone compound or its salt (hereinafter referred to as PQQ, which will be explained more fully below) is allowed to react with an α-amino acid, methylamine or the like in the presence of oxygen. The reaction is usually undertaken in a aqueous medium like a microbial culture. The pH of the reaction mixture is usually in the range from 2 to 10, and the reaction temperature is practically in the range from 20 to 100° C. The reaction time is preferably within 24 hours.

OPQs in the present invention include OPQ (R=H) obtained from a PQQ and any of glycine, threonine, tryptophan, proline, tyrosine, serine, and monomethylamine [Japanese Patent Publication (Laid-Open) No. 294281/1991]; hydroxymethyl-OPQ obtained from a PQQ and serine [Japanese Patent Publication (Laid-Open) No. 123782/1991]; 1-methyl-ethyl-OPQ obtained from a PQQ and valine [Japanese Patent Publication (Laid-Open) No. 170484/1991]; 1-methylpropyl-OPQ obtained from a PQQ and isoleucine [Japanese Patent Publication (Laid-Open) No. 170485/1991]; 2-methylpropyl-OPQ obtained from a PQQ and leucine [Japanese Patent Publication (Laid-Open) No. 170486/1991; methyl-OPQ obtained from a PQQ and alanine [Japanese Patent Publication (Laid-Open) No. 188081/1991]; 2-carboxyethyl-OPQ obtained from a PQQ and glutamic acid [Japanese Patent Publication (Laid-Open) No. 190882/1991]; 2-carbamoyl-ethyl-OPQ obtained from a PQQ and glutamine [Japanese Patent Publication (Laid-Open) No. 188082/1991]; 2-methyl-thioethyl-OPQ obtained from a PQQ and methionine [Japanese Patent Publication (Laid-Open) No. 19088/1991]; benzyl-OPQ obtained from a PQQ and phenylalanine [Japanese Patent Publication (Laid-Open) No. 190881/1991]; 4-hydroxy-phenylmethyl-OPQ obtained from a PQQ and tyrosine [Japanese Patent publication (Laid-Open) No. 9387/1992]; carboxymethyl-OPQ obtained from a PQQ and aspartic acid; carbamoylmethyl-OPQ obtained from a PQQ and asparagine; 4-imidazolylmethyl-OPQ obtained from a PQQ and histidine; 4-aminobutyl-OPQ obtained from a PQQ and lysine; 3-guanidinopropyl-OPQ obtained from a PQQ and arginine; and mercaptomethyl-OPQ obtained from a PQQ and cysteine. As shown above, R group of each of the OPQs basically corresponds to the R group of α-amino acid [R—CH(NH$_2$)COOH] which is used for substrate to produce one of OPQs. When tyrosine is used as the α-amino acid, OPQ (R=H) is the main product when the pH value of the reaction mixture is low and 4-hydroxyphenylmethyl OPQ (R=CH$_2$C$_4$H$_4$OH) is main product when the value is high.

Salts of these OPQs include alkaline metal salts, earth metal salts, ammonium salts and substituted ammonium salts, which are also effective as the NGF production accelerating agents. Typical examples are the salts of sodium, potassium, magnesium, calcium, ammonium, trimethylammonium, triethylammonium, and triethanolammonium.

Esters of these OPQs include those in which $R^1$, $R^2$ and $R^3$ in the formula mentioned above represent a hydrogen atom, or an alkyl, alkenyl, or benzyl group, which may be same or different, to form mono-, di- or triesters. These OPQs esters can be prepared by a conventional process wherein an OPQs or its salt is allowed to react with an alcohol. The alkyl group may be a methyl or ethyl group, and the alkenyl group may be an allyl group.

These objective OPQs esters can also be obtained by a conventional process wherein a PQQ or its salt is allowed to react with an alcohol to give the corresponding PQQ ester, and then the ester is allowed to react with an amino acid or methylamine.

PQQs have been found to function as a coenzyme for methanol dehydrogenase in methanol-metabolizing bacteria. The term, PQQS, used herein means 4,5-dihydro-4,5-dioxo-1H-pyrrolo[2,3-f]quinoline-2,7,9-tricarboxylic acid (PQQ) and its salts. The PQQs and their esters are represented by the following formula:

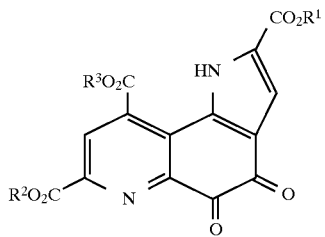

wherein in $R^1$, $R^2$ and $R^3$ represent a hydrogen or an alkyl, alkenyl, benzyl, propargyl or alkoxycarbonylalkyl group, which may be same or different.

PQQs and their esters actively accelerate NGF production, but they can not increase the NGF level in cerebral cortex, though they exhibit the production accelerating activity to sciatic nerve in animal experiments. Therefore, they are suitably used as therapeutic agents to prevent degeneration of the peripheral nervous system, such as peripheral nervous trauma and diabetic.

PQQs employed in this invention can be prepared by any of a number of known organic chemical syntheses [for example, that mentioned in J.A.C.S. Vol. 103, pages 5599–5600 (1981)] and fermentation methods [for example, that mentioned in Japanese Patent Publication (Laid-Open) No. 218597/1989]. PQQs referred to in this invention means PQQ and its salts, such as sodium and potassium salts of PQQ.

In the above formula for PQQ esters, $R^1$, $R^2$ and $R^3$ represent a hydrogen atom, or alkyl, alkenyl, benzyl, propargyl or alkoxycarbomethyl group, which may be same or different, to form mono-, di- or triesters. The alkyl group may be a methyl or ethyl group, and the alkenyl group may be an allyl group.

PQQ triesters are readily synthesized by reaction of a PQQ with an alcohol [see, for example, Japanese Patent Publications (Laid-Open) Nos. 123781/1991 and 145492/1991]. PQQ monoesters or diesters can be obtained by partial hydrolysis of a PQQ triester under basic condition. PQQ diesters can also be obtained by reaction of a PQQ monoester with an alcohol under suitably selected reaction conditions of the temperature and the time.

OPQs and PQQs and their esters in this invention may be administered orally or non-orally. In case of oral administration, they may be administered in the form of conventional formulations such as capsules, tablets, and powders. In case of non-oral administration, the formulations may be those for injections and parenteral fluids. Sustained release formulations are also effective.

Dosage and dosing time vary depending on symptoms, ages, body weights, dosing formulations, and others, but they may be administered ordinarily in an amount of 1–500 mg a day for adults in case of oral administration, or 0.1–100 mg in one or several dosage units per day in the case of non-oral administration.

In preparing formulations of the active ingredients of this invention, any additives, such as surface active agents, excipients, coloring agents, preservatives, coating auxiliaries, and the like may be suitably used. They may also be used in combination with other pharmaceuticals.

The following non-limiting examples illustrate the NGF production accelerating activity of PQQs, OPQs and their esters, according to the present invention.

EXAMPLE 1

L–M cells of fibroblast cell line originated from a mouse connective tissue were suspended in a 199 culturing medium (manufactured by Flow Laboratories) containing 0.5% peptone (manufactured by Difco Laboratories), and the suspension was placed in a microplate with 96 flat bottom holes to make the cell numbers of $2 \times 10^4$ /hole, which was then incubated in a $CO_2$ incubator (at 37° C., in an atmosphere of 5% $CO_2$ and 95% air) for 3 days. Each incubated liquid was replaced by a 199 medium containing OPQ of each given concentration and 0.5% bovine serum albumin (manufactured by Armour Pharmaceutical) or the same medium containing no OPQ, and incubated in a $CO_2$ incubator.

After 24 hour incubation, the amount of NGF contained in the supernatant fluid was estimated by enzyme immunoassay [see Korsching and Thoenen, Proc. Natl. Acad. Sci., U.S.A., 80, 3513–3516, (1983)]. The results are shown in Table 1.

TABLE 1

| Amount of OPQ added (μg/ml) | Amount of NGF produced (pg/ml) | Relative activity (%) |
| --- | --- | --- |
| 0 | 170 | 100 |
| 3.1 | 203 | 119 |
| 6.3 | 278 | 164 |
| 12.5 | 371 | 218 |
| 25 | 367 | 216 |
| 50 | 422 | 248 |
| 100 | 288 | 169 |

NGF assay

A solution of anti-mouse β-NGF antibody (made by using β-NGF prepared from mouse submaxillary gland as antigen) was dispensed to each hole on a 96 hole microplate made of polystyrene (MS-3496F, manufactured by Sumitomo Bakelite Co. Ltd.) in an amount of 50 μl/hole, and stood for 4 hours at 37° C. The antibody not adsorbed to each hole of the microplate was removed, and each hole was rinsed 3 times with a cleansing liquor. A solution of standard α-NGF (manufactured by Toyobo Co., Ltd.) or a sample solution was dispensed to each hole in an amount of 40 μl/hole, and stood for 18 hours at 4° C. Then, the standard α-NGF or sample solution (incubated supernatant as mentioned above) was removed, and each hole was rinsed 3 times. A solution of anti-β-NGF monoclonal antibody labeled with β-glactosidase (manufactured by Boehringer Mannheim) (40 mU/ml, pH 7.6) was dispensed to each hole in an amount of 50 μl/hole, and stood for 4 hours at 37° C. Then, the enzyme-labeled antibody was removed, and each hole was rinsed 3 times. A solution of 4-methyl-umbelliferyl-β-D-galactoside (manufactured by Sigma) was dispensed to each hole in an amount of 100 μg/hole, and allowed to react for 1.5 hours at room temperature, and then a 0.2M glycine-sodium hydroxide buffer (pH 10.3) was dispensed to each hole in an amount of 100 μl/hole to stop the enzyme reaction. Fluorescent intensity of 4-methylumbelliferone produced was estimated using a plate reader, and NGF amount was calculated from the standard curve. The results are shown in Table 1. NGF production accelerating activity of the tested compound was shown as a relative value (%) of the NGF amount produced by cells treated with the testing compound against the NGF amount produced by untreated cells without testing compound.

EXAMPLE 2

Procedure of Example 1 was repeated using hydroxymethyl-OPQ, in place of OPQ, to estimate its NGF production accelerating activity. The results are shown in Table 2.

TABLE 2

| Amount of hydroxy-methyl-OPQ added (μg/ml) | Amount of NGF produced (pg/ml) | Relative activity (%) |
|---|---|---|
| 0 | 384 | 100 |
| 0.8 | 525 | 137 |
| 1.6 | 554 | 144 |
| 3.1 | 565 | 147 |
| 6.3 | 582 | 152 |
| 12.5 | 593 | 154 |
| 25 | 670 | 174 |
| 50 | 708 | 184 |
| 100 | 786 | 205 |
| 200 | 982 | 258 |
| 400 | 1,453 | 378 |

EXAMPLE 3

Procedure of Example 1 was repeated using methyl-OPQ, in place of OPQ, to estimate its NGF production accelerating activity. The results are shown in Table 3.

TABLE 3

| Amount of methyl-OPQ added (μg/ml) | Amount of NGF produced (pg/ml) | Relative activity (%) |
|---|---|---|
| 0 | 384 | 100 |
| 0.8 | 525 | 137 |
| 1.6 | 604 | 157 |
| 3.1 | 599 | 156 |
| 6.3 | 665 | 173 |
| 12.5 | 665 | 173 |
| 25 | 632 | 165 |
| 50 | 676 | 176 |
| 100 | 681 | 177 |
| 200 | 873 | 227 |
| 400 | 1,075 | 280 |

EXAMPLE 4

Procedure of Example 1 was repeated using 2-carboxyethyl-OPQ, in place of OPQ, to estimate its NGF production accelerating activity. The results are shown in Table 4.

TABLE 4

| Amount of 2-carboxy-ethyl-OPQ added (μg/ml) | Amount of NGF produced (pg/ml) | Relative activity (%) |
|---|---|---|
| 0 | 264 | 100 |
| 1.6 | 330 | 125 |
| 3.1 | 387 | 147 |
| 6.3 | 330 | 125 |
| 12.5 | 349 | 132 |
| 25 | 356 | 135 |
| 50 | 368 | 139 |
| 100 | 381 | 144 |
| 200 | 381 | 144 |
| 400 | 454 | 172 |

EXAMPLE 5

Procedure of Example 1 was repeated using benzyl-OPQ, in place of OPQ, to estimate its NGF production accelerating activity. The results are shown in Table 5.

TABLE 5

| Amount of benzyl-OPQ added (μg/ml) | Amount of NGF produced (pg/ml) | Relative activity (%) |
|---|---|---|
| 0 | 264 | 100 |
| 1.6 | 375 | 142 |
| 3.1 | 368 | 139 |
| 6.3 | 375 | 142 |
| 12.5 | 349 | 132 |
| 25 | 375 | 142 |
| 50 | 356 | 135 |
| 100 | 317 | 120 |
| 200 | 298 | 113 |
| 400 | 271 | 103 |

EXAMPLE 6

Procedure of Example 1 was repeated using 1-methylpropyl-OPQ, in place of OPQ, to estimate its NGF production accelerating activity. The results are shown in Table 6.

TABLE 6

| Amount of 1-methyl-propyl-OPQ added (μg/ml) | Amount of NGF produced (pg/ml) | Relative activity (%) |
|---|---|---|
| 0 | 264 | 100 |
| 1.6 | 442 | 167 |
| 3.1 | 446 | 177 |
| 6.3 | 430 | 163 |
| 12.5 | 418 | 158 |
| 25 | 484 | 183 |
| 50 | 430 | 163 |
| 100 | 381 | 144 |
| 200 | 337 | 128 |
| 400 | 245 | 93 |

EXAMPLE 7

Procedure of Example 1 was repeated using 2-methylpropyl-OPQ, in place of OPQ, to estimate its NGF production accelerating activity. The results are shown in Table 7.

TABLE 7

| Amount of 2-methyl-propyl-OPQ added (μg/ml) | Amount of NGF produced (pg/ml) | Relative activity (%) |
| --- | --- | --- |
| 0 | 264 | 100 |
| 1.6 | 460 | 174 |
| 3.1 | 400 | 152 |
| 6.3 | 460 | 174 |
| 12.5 | 424 | 161 |
| 25 | 436 | 165 |
| 50 | 478 | 181 |
| 100 | 418 | 158 |
| 200 | 393 | 149 |
| 400 | 324 | 123 |

EXAMPLE 8

Procedure of Example 1 was repeated using 2-methylthioethyl-OPQ, in place of OPQ, to estimate its NGF production accelerating activity. The results are shown in Table 8.

TABLE 8

| Amount of 2-methyl-thioethyl-OPQ added (μg/ml) | Amount of NGF produced (pg/ml) | Relative activity (%) |
| --- | --- | --- |
| 0 | 264 | 100 |
| 1.6 | 490 | 186 |
| 3.1 | 442 | 167 |
| 6.3 | 484 | 183 |
| 12.5 | 430 | 163 |
| 25 | 466 | 177 |
| 50 | 480 | 186 |
| 100 | 424 | 161 |
| 200 | 356 | 135 |
| 400 | 349 | 132 |

EXAMPLE 9

Procedure of Example 1 was repeated using 2-carbamoylethyl-OPQ, in place of OPQ, to estimate its NGF production accelerating activity. The results are shown in Table 9.

TABLE 9

| Amount of 2-carbamoyl-ethyl-OPQ added (μg/ml) | Amount of NGF produced (pg/ml) | Relative activity (%) |
| --- | --- | --- |
| 0 | 382 | 100 |
| 0.8 | 443 | 116 |
| 1.6 | 512 | 134 |
| 3.1 | 505 | 132 |
| 6.3 | 546 | 143 |
| 12.5 | 632 | 165 |
| 25 | 639 | 167 |
| 50 | 652 | 171 |
| 100 | 566 | 148 |
| 200 | 512 | 134 |
| 400 | 408 | 107 |

EXAMPLE 10

Procedure of Example 1 was repeated using 1-methylethyl-OPQ, in place of OPQ, to estimate its NGF production accelerating activity. The results are shown in Table 10.

TABLE 10

| Amount of 1-methyl-ethyl-OPQ added (μg/ml) | Amount of NGF produced (pg/ml) | Relative activity (%) |
| --- | --- | --- |
| 0 | 382 | 100 |
| 0.8 | 386 | 101 |
| 1.6 | 478 | 125 |
| 3.1 | 492 | 129 |
| 6.3 | 526 | 138 |
| 12.5 | 546 | 143 |
| 25 | 553 | 145 |
| 50 | 606 | 159 |
| 100 | 573 | 150 |
| 200 | 539 | 141 |
| 400 | 485 | 127 |

EXAMPLE 11

Procedure of Example 1 was repeated using 4-hydroxyphenylmethyl-OPQ, in place of OPQ, to estimate its NGF production accelerating activity. The results are shown in Table 11.

TABLE 11

| Amount of 4-hydrozy-phenylmethyl-OPQ added (μg/ml) | Amount of NGF produced (pg/ml) | Relative activity (%) |
| --- | --- | --- |
| 0 | 382 | 100 |
| 0.8 | 560 | 147 |
| 1.6 | 580 | 152 |
| 3.1 | 553 | 145 |
| 6.3 | 632 | 165 |
| 12.5 | 613 | 160 |
| 25 | 613 | 160 |
| 50 | 652 | 171 |
| 100 | 429 | 112 |
| 200 | 335 | 88 |

EXAMPLE 12

Procedure of Example 1 was repeated using OPQ methyl ester at 2-position (OPQ-2-ME), in place of OPQ, to estimate its NGF production accelerating activity. The results are shown in Table 12.

TABLE 12

| Amount of OFQ-2-ME added (μg/ml) | Amount of NGF produced (pg/ml) | Relative activity (%) |
| --- | --- | --- |
| 0 | 259 | 100 |
| 0.8 | 290 | 112 |
| 1.6 | 299 | 115 |
| 3.1 | 299 | 115 |
| 6.3 | 344 | 133 |
| 12.5 | 308 | 119 |
| 25 | 234 | 90 |

EXAMPLE 13

Procedure of Example 1 was repeated using OPQ methyl ester at 7-position (OPQ-7-ME), in place of OPQ, to estimate its NGF production accelerating activity. The results are shown in Table 13.

TABLE 13

| Amount of OPQ-7-ME added (μg/ml) | Amount of NGF produced (pg/ml) | Relative activity (%) |
| --- | --- | --- |
| 0 | 219 | 100 |
| 0.8 | 217 | 99 |
| 1.6 | 265 | 121 |
| 3.1 | 242 | 111 |
| 6.3 | 234 | 107 |
| 12.5 | 235 | 107 |
| 25 | 266 | 121 |

EXAMPLE 14

Procedure of Example 1 was repeated using OPQ dimethyl ester at 2- and 7-positions (OPQ-2,7-DME), in place of OPQ, to estimate its NGF production accelerating activity. The results are shown in Table 14.

TABLE 14

| Amount of OPQ-2,7-DME added (μg/ml) | Amount of NGF produced (pg/ml) | Relative activity (%) |
| --- | --- | --- |
| 0 | 259 | 100 |
| 0.8 | 299 | 115 |
| 1.6 | 345 | 133 |
| 3.1 | 336 | 130 |
| 6.3 | 317 | 122 |
| 12.5 | 326 | 126 |
| 25 | 274 | 106 |

EXAMPLE 15

Procedure of Example 1 was repeated using OPQ dimethyl ester at 2- and 9-positions (OPQ-2,9-DME), in place of OPQ, to estimate its NGF production accelerating activity. The results are shown in Table 15.

TABLE 15

| Amount of OPQ-2,9-DME added (μg/ml) | Amount of NGF produced (pg/ml) | Relative activity (%) |
| --- | --- | --- |
| 0 | 259 | 100 |
| 0.8 | 249 | 96 |
| 1.6 | 290 | 112 |
| 3.1 | 342 | 132 |
| 6.3 | 373 | 144 |
| 12.5 | 435 | 168 |
| 25 | 393 | 152 |
| 50 | 258 | 100 |

EXAMPLE 16

Procedure of Example 1 was repeated using OPQ trimethyl ester (OPQ-TME), in place of OPQ, to estimate its NGF production accelerating activity. The results are shown in Table 16.

TABLE 16

| Amount of OPQ-TME added (μg/ml) | Amount of NGF produced (pg/ml) | Relative activity (%) |
| --- | --- | --- |
| 0 | 336 | 100 |
| 0.8 | 508 | 151 |
| 1.6 | 677 | 201 |
| 3.1 | 636 | 189 |
| 6.3 | 628 | 187 |
| 12.5 | 653 | 194 |
| 25 | 563 | 168 |
| 50 | 524 | 156 |
| 100 | 516 | 154 |
| 200 | 587 | 175 |
| 400 | 508 | 151 |

EXAMPLE 17

Procedure of Example 1 was repeated using OPQ 2-methyl-7,9-diethyl ester (OPQ-2-ME-7,9-DEE), in place of OPQ, to estimate its NGF production accelerating activity. The results are shown in Table 17.

TABLE 17

| Amount of OPQ-2-ME-7,9-DEE added (μg/ml) | Amount of NGF produced (pg/ml) | Relative activity (%) |
| --- | --- | --- |
| 0 | 381 | 100 |
| 0.8 | 476 | 125 |
| 1.6 | 558 | 146 |
| 3.1 | 542 | 142 |
| 6.3 | 576 | 151 |
| 12.5 | 716 | 188 |
| 25 | 625 | 164 |
| 50 | 608 | 160 |
| 100 | 421 | 110 |

EXAMPLE 18

Procedure of Example 1 was repeated using $PQQ \cdot Na_2$, in place of OPQ, to estimate its NGF production accelerating activity. The results are shown in Table 18.

TABLE 18

| Amount of $PQQ \cdot Na_2$ added (μg/ml) | Amount of NGF produced (pg/ml) | Relative activity (%) |
| --- | --- | --- |
| 0 | 204 | 100 |
| 0.8 | 319 | 156 |
| 1.6 | 302 | 148 |
| 3.1 | 398 | 195 |
| 6.3 | 677 | 332 |
| 12.5 | 1,076 | 527 |
| 25 | 2,515 | 1,233 |
| 50 | 5,915 | 2,900 |
| 100 | 8,034 | 3,938 |
| 200 | 5,428 | 2,661 |
| 400 | 2,487 | 1,219 |

EXAMPLE 19

Procedure of Example 1 was repeated using PQQ dipotassium salt ($PQQ \cdot K_2$), in place of OPQ, to estimate its NGF production accelerating activity. The results are shown in Table 19.

TABLE 19

| Amount of PQQ.K$_2$ added ($\mu$g/ml) | Amount of NGF produced (pg/ml) | Relative activity (%) |
|---|---|---|
| 0 | 384 | 100 |
| 0.8 | 560 | 146 |
| 1.6 | 554 | 144 |
| 3.1 | 729 | 190 |
| 6.3 | 812 | 211 |
| 12.5 | 1,453 | 378 |
| 25 | 3,288 | 856 |
| 50 | 7,047 | 1,835 |
| 100 | 7,281 | 1,896 |
| 200 | 4,425 | 1,152 |
| 400 | 1,237 | 322 |

EXAMPLE 20

Procedure of Example 1 was repeated using PQQ methyl ester at 2-position (PQQ-2-ME), in place of OPQ, to estimate its NGF production accelerating activity. The results are shown in Table 20.

TABLE 20

| Amount of PQQ-2-ME added ($\mu$g/ml) | Amount of NGF produced (pg/ml) | Relative activity (%) |
|---|---|---|
| 0 | 727 | 100 |
| 0.8 | 1,434 | 197 |
| 1.6 | 1,663 | 229 |
| 3.1 | 2,501 | 344 |
| 6.3 | 3,126 | 430 |
| 12.5 | 4,510 | 620 |
| 25 | 5,611 | 772 |
| 50 | 5,188 | 714 |
| 100 | 2,397 | 330 |

EXAMPLE 21

Procedure of Example 1 was repeated using PQQ methyl ester at 7-position (PQQ-7-ME), in place of OPQ, to estimate its NGF production accelerating activity. The results are shown in Table 21.

TABLE 21

| Amount of PQQ-7-ME added ($\mu$g/ml) | Amount of NGF produced (pg/ml) | Relative activity (%) |
|---|---|---|
| 0 | 219 | 100 |
| 1.6 | 258 | 118 |
| 3.1 | 282 | 129 |
| 6.3 | 493 | 225 |
| 12.5 | 1,238 | 565 |
| 25 | 1,448 | 661 |
| 50 | 928 | 424 |
| 100 | 335 | 153 |
| 200 | 266 | 121 |

EXAMPLE 22

Procedure of Example 1 was repeated using PQQ dimethyl ester at 2- and 9-positions (PQQ-2,9-DME), in place of OPQ, to estimate its NGF production accelerating activity. The results are shown in Table 22.

TABLE 22

| Amount of PQQ-2,9-DME added ($\mu$g/ml) | Amount of NGF produced (pg/ml) | Relative activity (%) |
|---|---|---|
| 0 | 727 | 100 |
| 0.8 | 1,165 | 160 |
| 1.6 | 1,777 | 244 |
| 3.1 | 3,126 | 430 |
| 6.3 | 3,790 | 521 |
| 12.5 | 4,790 | 659 |
| 25 | 6,829 | 939 |
| 50 | 5,499 | 756 |
| 100 | 4,584 | 631 |
| 200 | 1,852 | 255 |

EXAMPLE 23

Procedure of Example 1 was repeated using POQ trimethyl ester (PQQ-TME), in place of OPQ, to estimate its NGF production accelerating activity. The results are shown in Table 23.

TABLE 23

| Amount of PQQ-TME added ($\mu$g/ml) | Amount of NGF produced (pg/ml) | Relative activity (%) |
|---|---|---|
| 0 | 341 | 100 |
| 0.8 | 429 | 126 |
| 1.6 | 464 | 136 |
| 3.1 | 600 | 176 |
| 6.3 | 954 | 280 |
| 12.5 | 1,448 | 425 |
| 25 | 2,852 | 836 |
| 50 | 3,015 | 884 |
| 100 | 1,678 | 492 |

EXAMPLE 24

Procedure of Example 1 was repeated using PQQ triethyl ester (PQQ-TEE), in place of OPQ, to estimate its NGF production accelerating activity. The results are shown in Table 24.

TABLE 24

| Amount of PQQ-TEE added ($\mu$g/ml) | Amount of NGF produced (pg/ml) | Relative activity (%) |
|---|---|---|
| 0 | 381 | 100 |
| 0.8 | 2,190 | 575 |
| 1.6 | 2,160 | 567 |
| 3.1 | 1,889 | 496 |
| 6.3 | 1,882 | 494 |
| 12.5 | 1,249 | 328 |
| 25 | 550 | 144 |

EXAMPLE 25

Procedure of Example 1 was repeated using PQQ triallyl ester (PQQ-TAE), in place of OPQ, to estimate its NGF production accelerating activity. The results are shown in Table 25.

TABLE 25

| Amount of PQQ-TAE added (μg/ml) | Amount of NGF produced (pg/ml) | Relative activity (%) |
| --- | --- | --- |
| 0 | 204 | 100 |
| 0.8 | 403 | 198 |
| 1.6 | 414 | 203 |
| 3.1 | 611 | 300 |
| 6.3 | 776 | 380 |
| 12.5 | 1,063 | 521 |
| 25 | 707 | 347 |

EXAMPLE 26

Procedure of Example 1 was repeated using PQQ tri-ethoxycarbonylmethyl ester (PQQ-TECE), in place of OPQ, to estimate its NGF production accelerating activity. The results are shown in Table 26.

TABLE 26

| Amount of PQQ-TECE added (μg/ml) | Amount of NGF produced (pg/ml) | Relative activity (%) |
| --- | --- | --- |
| 0 | 381 | 100 |
| 3.1 | 428 | 112 |
| 6.3 | 455 | 119 |
| 12.5 | 558 | 146 |
| 25 | 669 | 176 |
| 50 | 1,908 | 508 |
| 100 | 3,092 | 812 |
| 200 | 304 | 80 |

EXAMPLE 27

Procedure of Example 1 was repeated using PQQ tripropargyl ester (PQQ-TPGE), in place of OPQ, to estimate its NGF production accelerating activity. The results are shown in Table 27.

TABLE 27

| Amount of PQQ-TPGE added (μg/ml) | Amount of NGF produced (pg/ml) | Relative activity (%) |
| --- | --- | --- |
| 0 | 381 | 100 |
| 1.6 | 389 | 102 |
| 3.1 | 599 | 157 |
| 6.3 | 764 | 201 |
| 12.5 | 2,453 | 644 |
| 25 | 6,022 | 1,581 |
| 50 | 3,926 | 1,030 |
| 100 | 505 | 133 |

EXAMPLE 28

L–M cells were incubated in similar way as in Example 1 using epinephrine which has been known as an NGF production accelerator, in place of OPQ, to estimate its NGF production accelerating activity. The results are shown in Table 28.

TABLE 28

| Amount of epinephrine added (μg/ml) | Amount of NGF produced (pg/ml) | Relative activity (%) |
| --- | --- | --- |
| 0 | 179 | 100 |
| 0.8 | 180 | 101 |
| 1.6 | 168 | 94 |
| 3.1 | 180 | 101 |
| 6.3 | 187 | 104 |
| 12.5 | 224 | 125 |
| 25 | 319 | 178 |
| 50 | 431 | 241 |
| 100 | 872 | 487 |
| 200 | 259 | 144 |

Epinephrine showed NGF production accelerating activity at an amount of not less than 12.5 μg/ml, and exhibited the maximum value (about 500%) at an amount of 100 μg/ml. On the other hand, OPQs and OPQ esters showed almost the same degree of NGF production accelerating activity as shown in Examples 1–17. Also, PQQs and PQQ esters gave high activity values even at a lower concentration, having markedly higher NGF production accelerating activity, when compared with epinephrine.

EXAMPLE 29

L–M cells were incubated in similar way as in Example 1.

In three groups (A, B and C) of L–M cell incubation systems, Group A contained no tested compound, Group B contained 100 μg/ml of PQQ·$Na_2$, and Group C contained 275 μg/ml of epinephrine. Amounts of NGF produced during the course of times (3, 6, 9, 12, 24, 30, 36 and 48 hours from the beginning of incubation) were estimated. The results are shown in Table 29.

As obvious from the table, addition of PQQ·$Na_2$ definitely increases NGF production, as compared with the cases of no addition and adding epinephrine.

TABLE 29

| | Amount of NGF produced (pg/ml) | | |
| --- | --- | --- | --- |
| Incubating period of time (hr) | (A) No addition | (B) PQQ·$Na_2$ 100 μg/ml added | (C) Epinephrine 275 μg/ml added |
| 0 | 63 | 81 | 66 |
| 3 | 124 | 180 | 92 |
| 6 | 219 | 667 | 202 |
| 9 | 254 | 2,657 | 268 |
| 12 | 271 | 4,947 | 347 |
| 24 | 378 | 9,924 | 556 |
| 30 | 420 | 8,635 | 689 |
| 36 | 458 | 8,334 | 873 |
| 48 | 465 | 7,769 | 1,960 |

EXAMPLE 30

SD female rats (7 weeks age, 160–190 g) were put under anesthesia by intramuscularly administering 25 mg of ketamine hydrochloride and 0.25 mg of doloperidol. Left femor sciatic nerve was exposed and cut off, and the cut ends were connected with a gap of about 2 mm using a silicone tube (1 mm inner diameter, 6 mm length). The gap between the cut ends was filled with an isotonic sodium chloride solution. After reduction of the operational cut, each 0.5 ml of an aqueous 2% gum arabic solution containing a given concentration of OPQ was administered intraperitoneally. As control, 0.5 ml of an aqueous 2% gum arabic solution containing no OPQ was administered intraperitoneally. As for positive control, the gap of the cut ends of sciatic nerve was filled with an isotonic sodium chloride solution containing 1 mg/ml of NGF, and 0.5 ml of an aqueous 2% gum arabic solution containing no OPQ was administered intraperitoneally. After 4 weeks from the operation, animals were sacrificed by cervical bertebral luxation, and the reproduced sciatic nerves were collected. Cross sectional slices of the reproduced sciatic nerves were prepared and dyed with hematoxylin-eosine, and number of the reproduced nerve fibers was counted.

The results are shown in Table 30. As obvious from the table, number of the reproduced sciatic nerves was much increased by administering OPQ, which was comparable to direct injection of NGF.

TABLE 30

| Amount of OPQ administered ($\mu$g/kg rat) | Number of reproduced sciatic nerves | Relative activity (%) |
| --- | --- | --- |
| 0 | 12,590 | 100 |
| 5 | 12,600 | 100 |
| 10 | 12,848 | 102 |
| 50 | 13,912 | 111 |
| 100 | 19,839 | 158 |
| 500 | 17,870 | 142 |
| Positive control (NGF gap injection) | 20,932 | 166 |

EXAMPLE 31

Procedure of Example 30 was repeated using OPQ trimethyl ester (OPQ-TME), in place of OPQ, to estimate the reproduction accelerating activity of OPQ-TME for sciatic nerve. The results are shown in Table 31.

As obvious from the table, number of the reproduced sciatic nerves was much increased by administering OPQ-TME, which was comparable to NGF.

TABLE 31

| Amount of OPQ.TME administered ($\mu$g/kg rat) | Number of reproduced sciatic nerves | Relative activity (%) |
| --- | --- | --- |
| 0 | 12,590 | 100 |
| 5 | 11,860 | 94 |
| 10 | 11,193 | 89 |
| 50 | 12,780 | 102 |
| 100 | 22,966 | 182 |
| 500 | 26,313 | 209 |
| Positive control (NGF gap injection) | 20,932 | 166 |

EXAMPLE 32

Procedure of Example 30 was repeated using PQQ·Na$_2$, in place of OPQ, to estimate the reproduction accelerating activity for sciatic nerve. The results are shown in Table 32.

As obvious from the table, number of the reproduced sciatic nerves was much increased by administering OPQ-Na$_2$, which was comparable to NGF.

TABLE 32

| Amount of PQQ.Na$_2$ administered ($\mu$g/kg rat) | Number of reproduced sciatic nerves | Relative activity (%) |
| --- | --- | --- |
| 0 | 12,590 | 100 |
| 5 | 16,984 | 135 |
| 10 | 21,822 | 173 |
| 50 | 26,142 | 208 |
| 100 | 18,247 | 145 |
| 500 | 14,031 | 111 |
| Positive control (NGF gap injection) | 20,932 | 166 |

EXAMPLE 33

Procedure of Example 30 was repeated using PQQ trimethyl ester (PQQ-TME), in place of OPQ, to estimate its reproduction accelerating activity for sciatic nerve. The results are shown in Table 33.

As obvious from the table, number of the reproduced sciatic nerves was much increased by administering PQQ-TME, which was comparable to NGF.

TABLE 33

| Amount of PQQ-TME administered ($\mu$g/kg rat) | Number of reproduced sciatic nerves | Relative activity (%) |
| --- | --- | --- |
| 0 | 12,590 | 100 |
| 5 | 19,047 | 151 |
| 10 | 21,054 | 167 |
| 50 | 24,940 | 198 |
| 100 | 17,882 | 142 |
| 500 | 17,902 | 142 |
| Positive control (NGF gap injection) | 20,932 | 166 |

EXAMPLE 34

OPQ trimethyl ester (OPQ-TME) was suspended in 0.5 ml of an aqueous 2% gum arabica in a given concentration, and the suspension was administered to Wistar male rats (8–10 weeks age, 200–250 g) intraperitoneally. Administrations were conducted every other days once a day, 4 times in total. After 2 days from the last administration, rats were dissected under anesthesia, and the neocortex, submaxillary grand and hippocampus were collected. The following procedures were conducted under ice-cooling. Each of these tissues was weighed, and mixed with a 20 time-volume of a phosphate buffer (8 g/l of NaCl, 0.2 g/l of KCl, 1.15 g/l of Na$_2$HPO$_4$ and 0.2 g/l of KH2 PO$_4$), and the mixture was homogenized by an ultrasonic crusher, followed by centrifugation at 10,000×G for 30 minutes to separate the supernatant. Amount of NGF contained in the supernatant was estimated by enzyme immunoassay. The results are shown in Table 34. NGF amount (ng) per 1 mg (wet weight) of neocortex, submaxillary gland or hippocampus was set forth as the average value ± standard error from 3 heads tested simultaneously. As for former two tissues, relative activities were also shown against the case of no OPQ-TME administration.

As obvious from the table, NGF contents in neocortex and submaxillary gland were increased by administering OPT-TME. Particularly, the degree of increase was high in neocortex.

TABLE 34

| Amount of OPQ-TME administered (μg/kg rat) | Neocortex NGF (ng/mg tissue wet weight) | Relative activity (%) | Submaxillary gland NGF (ng/mg tissue wet weight) | Relative activity (%) | Hippocampus NGF (ng/mg tissue wet weight) |
|---|---|---|---|---|---|
| 0 | 1.83 ± 0.05 | 100 | 0.63 ± 0.04 | 100 | 2.44 ± 0.23 |
| 0.1 | 2.64 ± 0.17 | 144 | 0.70 ± 0.05 | 111 | 2.31 ± 0.20 |
| 0.5 | 2.60 ± 0.40 | 142 | 0.85 ± 0.06 | 135 | 2.20 ± 0.46 |
| 1.0 | 3.17 ± 0.44 | 173 | 0.67 ± 0.09 | 106 | — |

EXAMPLE 35

Procedure of Example 34 was repeated using PQQ trimethyl ester (PQQ-TME), in place of OPQ-TME, to estimate the accelerating activities of PQQ-TME for NGF contents of neocortex, submaxillary gland and hippocampus. The results are shown in Table 35.

Administration of PQQ-TME did not increase the NGF contents in neocortex, submaxillary gland and hippocampus. Supposedly, PQQ-TME have no NGF production accelerating activity to central nervous system.

TABLE 35

| Amount of PQQ-TME administered (mg/kg rat) | NGF production amount (ng/mg tissue wet weight) | | |
|---|---|---|---|
| | Neocortex | Submaxillary gland | Hippocampus |
| 0 | 2.51 ± 0.23 | 1.42 ± 0.07 | 2.53 ± 0.23 |
| 0.1 | 2.25 ± 0.10 | 1.67 ± 0.15 | 2.44 ± 0.04 |
| 0.5 | 2.19 ± 0.33 | 1.58 ± 0.07 | 2.10 ± 0.15 |
| 1.0 | 2.71 ± 0.30 | 1.30 ± 0.08 | — |

Thus, as OPQs and their esters exhibit NGF production accelerating activity, and, in animal experiments, they increase the NGF content in neocortex, and accelerate reproduction of sciatic nerve, the nerve growth factor production accelerators of the present invention are suitably utilized as preventive and therapeutic agents for functional disorders of central nervous system, particularly, Alzheimer's dementia, cerebral ischemia and spinal trauma, as well as for functional disorders of peripheral nervous system, particularly, peripheral nervous system trauma and diabetic neuropathy.

Further, as PQQs and their esters exhibit strong NGF production accelerating activity, and, in animal experiments, they accelerate the reproduction of sciatic nerve, the present accelerators are suitably utilized as preventing and treating agents for functional disorders of peripheral nervous system, particularly, peripheral nervous system trauma, diabetic neuropathy, etc.

What we claim is:

1. A method for accelerating the production of nerve growth factor in a non-diabetic patient under treatment for degeneration of the central or peripheral nervous system which comprises administration to said patient of a pyrroloquinolinequinone compound and/or its ester of the formula:

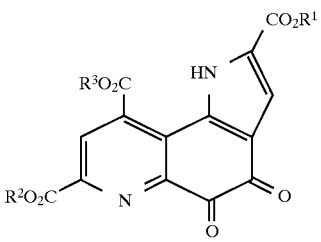

wherein $R^1$, $R^2$ and $R^3$ are each independently selected from the group consisting of hydrogen atom, alkyl, alkenyl, benzyl, propargyl and alkoxycarbonylalkyl group, in an amount effective to accelerate such production.

2. The method according to claim 1 wherein the compound is pyrroloquinolinequinone disodium salt.

3. The method according to claim 1 wherein the compound is pyrroloquinolinequinone dipotassium salt.

4. The method according to claim 1 wherein the compound is pyrroloquinolinequinone 2-methyl ester.

5. The method according to claim 1 wherein the compound is pyrroloquinolinequinone 7-methyl ester.

6. The method according to claim 1 wherein the compound is pyrroloquinolinequinone 2,9-dimethyl ester.

7. The method according to claim 1 wherein the compound is pyrroloquinolinequinone 2,7,9-trimethyl ester.

8. The method according to claim 1 wherein the compound is pyrroloquinolinequinone 2 7,9-triethyl ester.

9. The method according to claim 1 wherein the compound is pyrroloquinolinequinone 2,7,9-triallyl ester.

10. The method according to claim 1 wherein the compound is pyrroloquinolinequinone 2,7,9-triethoxycarbonylmethyl ester.

11. The method according to claim 1 wherein the compound is pyrroloquinolinequinone 2,7,9-tripropargyl ester.

* * * * *